US011298257B2

(12) United States Patent
Fernandez et al.

(10) Patent No.: US 11,298,257 B2
(45) Date of Patent: Apr. 12, 2022

(54) OSTOMY APPARATUSES AND RELATED METHODS

(71) Applicant: 3 West C, LLC, Tyler, TX (US)

(72) Inventors: Luis Fernandez, Tyler, TX (US); Charles Gordon, Tyler, TX (US)

(73) Assignee: 3 WEST C, LLC., Tyler, TX (US)

( * ) Notice: Subject to any disclaimer, the term of this patent is extended or adjusted under 35 U.S.C. 154(b) by 972 days.

(21) Appl. No.: 15/928,642

(22) Filed: Mar. 22, 2018

(65) Prior Publication Data

US 2018/0271694 A1 Sep. 27, 2018

Related U.S. Application Data

(60) Provisional application No. 62/475,057, filed on Mar. 22, 2017.

(51) Int. Cl.
| | |
|---|---|
| *A61F 5/44* | (2006.01) |
| *A61F 5/443* | (2006.01) |
| *A61F 5/448* | (2006.01) |
| *A61M 1/00* | (2006.01) |
| *A61F 5/442* | (2006.01) |

(52) U.S. Cl.
CPC ............ *A61F 5/4401* (2013.01); *A61F 5/442* (2013.01); *A61F 5/443* (2013.01); *A61F 5/4405* (2013.01); *A61F 5/448* (2013.01); *A61M 1/90* (2021.05); *A61F 2005/4486* (2013.01)

(58) Field of Classification Search
CPC ...... A61F 5/4401; A61F 5/4405; A61F 5/442; A61F 5/443; A61F 5/448; A61F 2005/4486; A61M 1/0088
See application file for complete search history.

(56) References Cited

U.S. PATENT DOCUMENTS

| | | | | |
|---|---|---|---|---|
| 4,439,162 | A * | 3/1984 | Blaine | G09B 23/34 434/268 |
| 4,518,389 | A | 5/1985 | Steer et al. | |
| 4,553,967 | A | 11/1985 | Ferguson et al. | |
| 4,648,875 | A * | 3/1987 | Ferguson | A61F 5/448 604/339 |
| 4,834,732 | A * | 5/1989 | Steer | A61F 5/448 604/338 |
| 4,929,245 | A * | 5/1990 | Holtermann | A61F 5/448 604/338 |
| 5,041,102 | A * | 8/1991 | Steer | A61F 5/448 604/338 |
| 5,180,377 | A | 1/1993 | Holtermann | |
| 5,250,042 | A | 10/1993 | Torgalkar et al. | |

(Continued)

OTHER PUBLICATIONS

International Search Report and Written Opinion issued in PCT/US2014/057725 dated Feb. 24, 2015.

*Primary Examiner* — Guy K Townsend
(74) *Attorney, Agent, or Firm* — Norton Rose Fulbright US LLP

(57) ABSTRACT

An ostomy apparatus comprising a flexible container having an interior chamber for receiving waste from a patient's stoma and an opening for surrounding the stoma, a housing coupled to the container, wherein the housing is configured to accommodate an absorbent material that surrounds the stoma, a port configured to provide fluid communication between the housing and a pressure source; and an adhesive layer configured to seal the housing to skin around the stoma.

19 Claims, 3 Drawing Sheets

(56) References Cited

U.S. PATENT DOCUMENTS

| | | |
|---|---|---|
| 5,322,526 A | 6/1994 | Nakamura et al. |
| 5,693,035 A | 12/1997 | Leise et al. |
| 5,961,501 A | 10/1999 | Cassidy et al. |
| 6,312,415 B1 | 11/2001 | Nielsen et al. |
| 6,409,710 B1 | 6/2002 | Holtermann |
| 6,451,883 B1 | 9/2002 | Chen et al. |
| 6,506,184 B1 * | 1/2003 | Villefrance ............ A61F 5/441 604/333 |
| 6,569,134 B1 | 5/2003 | Leise et al. |
| 6,712,800 B2 | 3/2004 | Kanbara |
| 6,773,420 B2 * | 8/2004 | Kanbara ................ A61F 5/441 604/333 |
| 7,087,041 B2 * | 8/2006 | von Dyck ............... A61F 5/442 604/332 |
| 7,789,866 B2 | 9/2010 | Poulsen et al. |
| 7,927,320 B2 * | 4/2011 | Goldwasser .......... A61F 13/505 604/344 |
| 8,007,483 B2 | 8/2011 | Worsoee |
| 8,142,406 B2 * | 3/2012 | Blum .................... A61F 5/445 604/338 |
| 8,758,314 B2 * | 6/2014 | Hall ...................... A61F 5/445 604/319 |
| 8,771,243 B2 * | 7/2014 | Khan .................... A61F 5/449 604/313 |
| 2003/0028161 A1 | 2/2003 | Caballo |
| 2003/0060786 A1 | 3/2003 | Olsen et al. |
| 2004/0171999 A1 | 9/2004 | Andersen et al. |
| 2006/0184145 A1 | 8/2006 | Ciok et al. |
| 2008/0071237 A1 | 3/2008 | Chen et al. |
| 2008/0262446 A1 | 10/2008 | Ryder et al. |
| 2008/0287892 A1 * | 11/2008 | Khan ..................... A61M 1/69 604/313 |
| 2009/0234313 A1 | 9/2009 | Mullejeans et al. |
| 2010/0137821 A1 * | 6/2010 | Hansen ................. A61F 5/4404 604/338 |
| 2010/0145292 A1 * | 6/2010 | Mayer .................... A61F 5/445 604/337 |
| 2010/0160875 A1 * | 6/2010 | James ................... A61M 1/0001 604/319 |
| 2010/0168693 A1 | 7/2010 | Edvardsen et al. |
| 2011/0213322 A1 | 9/2011 | Cramer et al. |
| 2012/0101458 A1 * | 4/2012 | Hall ........................ A61M 1/90 604/319 |
| 2013/0053797 A1 * | 2/2013 | Locke .................... A61M 27/00 604/319 |
| 2013/0053798 A1 * | 2/2013 | Coulthard ............. A61M 27/00 604/319 |
| 2013/0060214 A1 | 3/2013 | Willoughby et al. |
| 2013/0138062 A1 | 5/2013 | Klein et al. |
| 2013/0253455 A1 | 9/2013 | Masters et al. |
| 2014/0148770 A1 | 5/2014 | Masters et al. |
| 2015/0094675 A1 | 4/2015 | Kyvic et al. |
| 2015/0190198 A1 | 7/2015 | Debel et al. |
| 2015/0265455 A1 * | 9/2015 | Fernandez ............ A61F 5/448 604/342 |
| 2017/0157284 A1 * | 6/2017 | Pearce ................. A61L 24/046 |
| 2018/0271694 A1 * | 9/2018 | Fernandez ........... A61F 5/4401 604/333 |

* cited by examiner

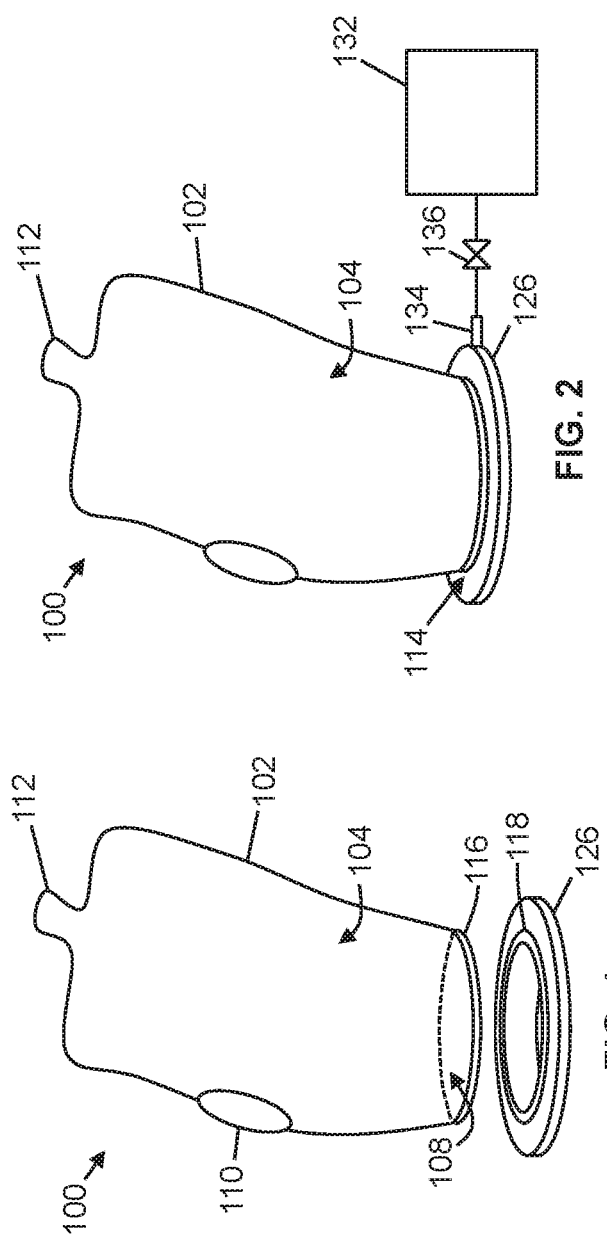
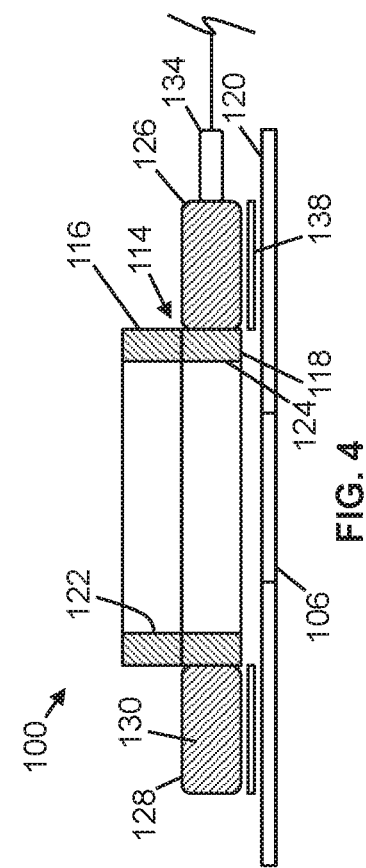
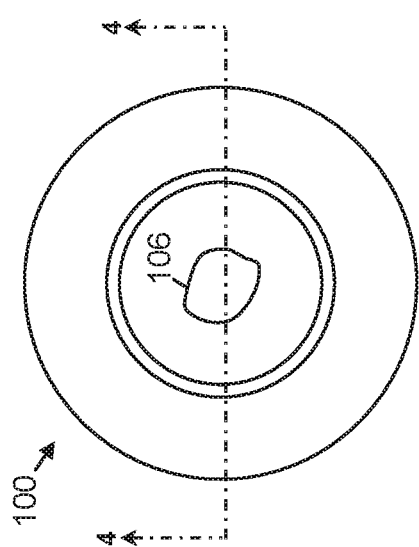

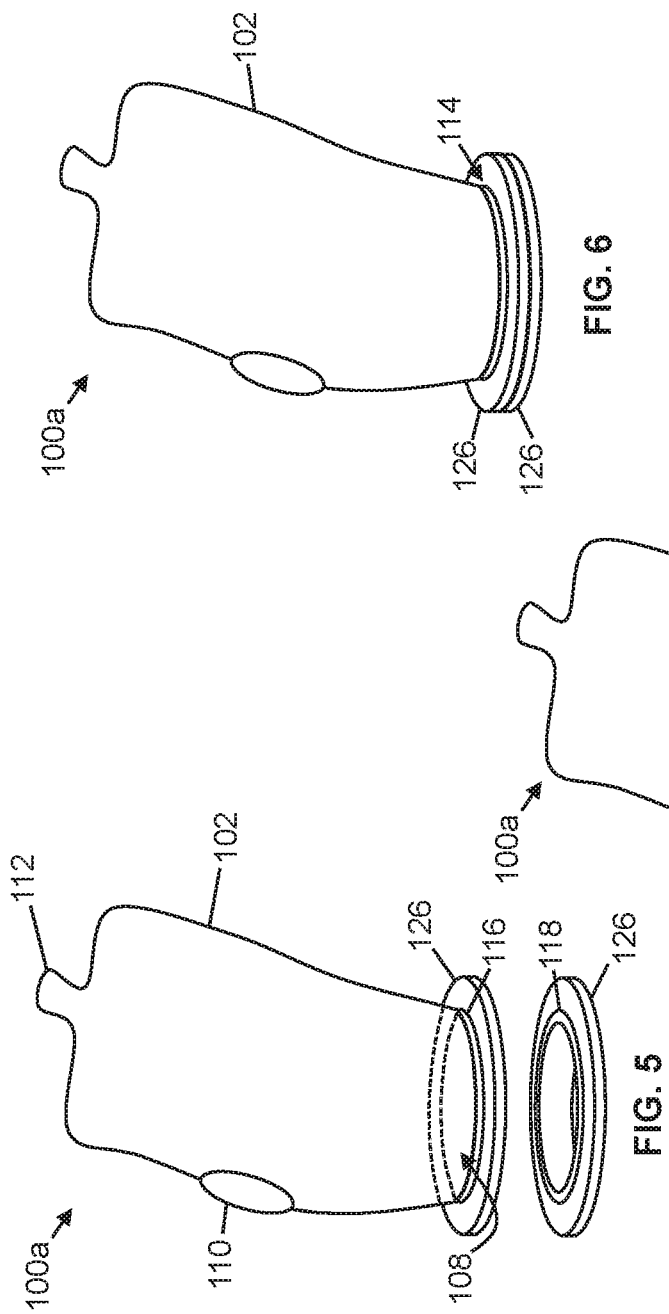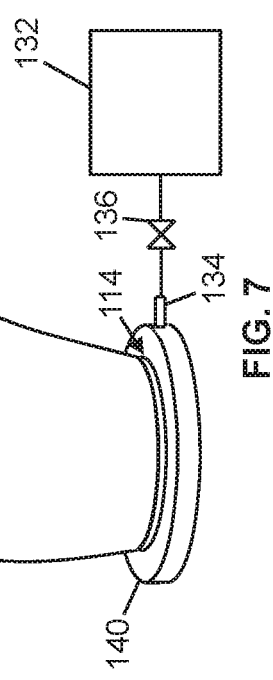

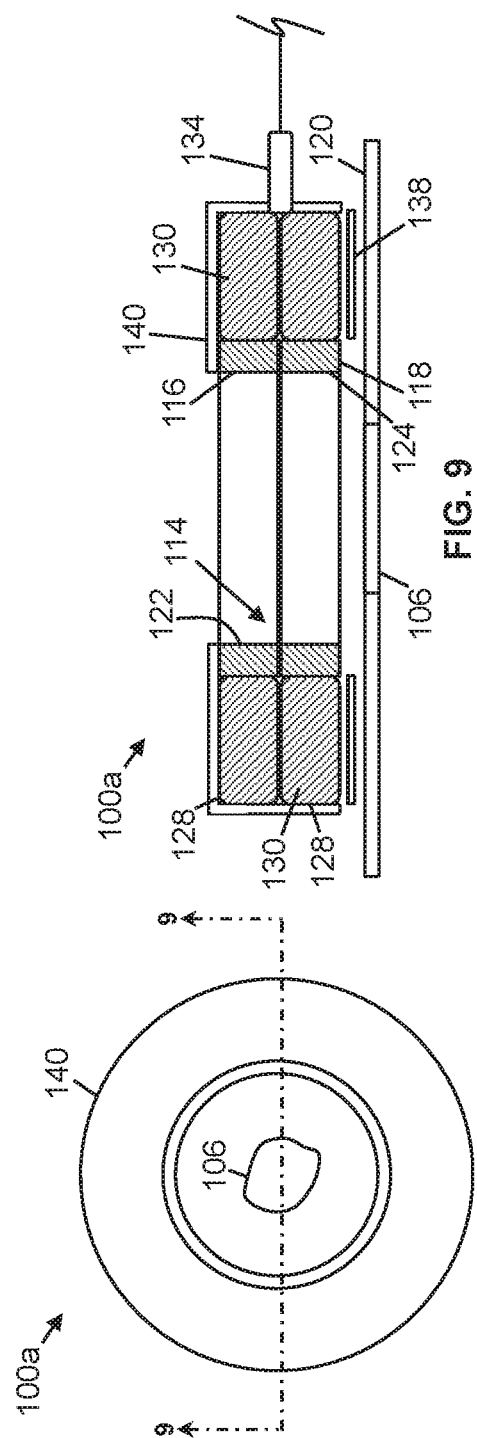

OSTOMY APPARATUSES AND RELATED METHODS

CROSS-REFERENCE TO RELATED APPLICATIONS

This application claims priority to U.S. Provisional Application No. 62/475,057, the entire contents of which is specifically incorporated by reference herein without disclaimer.

BACKGROUND OF THE INVENTION

1. Field of the Invention

The present invention relates generally to ostomy apparatuses, and more particularly, but not by way of limitation, to ostomy apparatuses for receiving waste from a patient's stoma.

2. Description of Related Art

An ostomy is a surgical procedure to create an opening (e.g., a stoma) from an area inside the body to the outside. It is used to treat certain diseases of the digestive or urinary systems. It can be permanent or temporary. Three common ostomies are a colostomy, an ileostomy and a urostomy. In a colostomy, a stoma is formed in a patient's abdominal wall and the colon is attached to the stoma. In an ileostomy, a stoma is formed in a patient's abdominal wall and the bottom of the small intestine (i.e., the ileum) is attached to the stoma. In a urostomy, a stoma is formed in a patient's abdominal wall and a passage is created to allow urine to flow outside of the body.

Waste is discharged from the stoma, and the patient must wear an ostomy bag to collect the waste material. A wide variety of ostomy bags are in general use today. However, these bags suffer from various issues and there is a need for an improved ostomy bag.

SUMMARY OF THE INVENTION

Some embodiments of the present ostomy apparatuses comprise a flexible container having: a first chamber for receiving waste from a patient's stoma; an opening for surrounding the stoma; and a second chamber configured to accommodate an absorbent material; and a pressure source configured to provide a sub-atmospheric pressure within the second chamber.

Some embodiments of the present ostomy apparatuses comprise a flexible container having an interior chamber for receiving waste from a patient's stoma and an opening for surrounding the stoma; a housing coupled to the container, wherein the housing is configured to accommodate an absorbent material that surrounds the stoma; a port configured to provide fluid communication between the housing and a pressure source; and an adhesive layer configured to seal the housing to skin around the stoma.

In some embodiments, the port is isolated from fluid communication with the interior chamber of the container.

Some embodiments of the present ostomy apparatuses comprise a flexible container having an interior chamber for receiving waste from a patient's stoma and an opening for surrounding the stoma; a housing coupled to the container, wherein the housing defines a chamber surrounding the stoma; an absorbent material configured to be disposed within the chamber of the housing; a pressure source in fluid communication with the absorbent material; an adhesive layer configured to provide a seal between the housing and skin surrounding the stoma.

In some embodiments, the pressure source is configured to provide a sub-atmospheric pressure within the chamber of the housing. In some embodiments, the pressure source is configured to provide a sub-atmospheric pressure on the absorbent material such that the absorbent material removes fluid from skin surrounding the stoma. In some embodiments, the pressure source comprises an electric pump. In some embodiments, the pressure source comprises a manual pump.

Some embodiments of the present ostomy apparatuses comprise a valve being configured to control fluid communication between the housing and the pressure source.

Some embodiments of the present ostomy apparatuses comprise a finger probe coupled to the flexible container, the finger probe being configured to allow a user to manipulate the stoma.

In some embodiments, the container has a resealable opening for draining the container. In some embodiments, the flexible container is a bag.

In some embodiments, the absorbent material includes an open cell structure. In some embodiments, the open cell structure comprises a sponge.

Some embodiments of the present ostomy apparatuses comprise a locking assembly configured to be coupled to the opening of the flexible container. In some embodiments, the locking assembly is configured to be coupled to the housing. In some embodiments, the locking assembly includes: a stoma lock assembly configured to be coupled to the housing, the stoma lock assembly having an opening therethrough; and a container lock assembly configured to be coupled to the container such that the container lock assembly seals the opening of the container to the stoma lock assembly.

Some embodiments of the present methods of collecting waste from a stoma of a patient comprise adhering an adhesive layer to skin surrounding the stoma; coupling a housing to the adhesive layer, the housing including: a chamber; and an absorbent material disposed within the chamber; coupling a flexible container to the housing, wherein the flexible container includes an interior chamber for receiving waste from the stoma and an opening for surrounding at least a portion of the stoma; communicating fluid between the chamber of the housing and a pressure source such that pressure within the chamber of the housing is sub-atmospheric.

In some embodiments of the present methods, the adhesive layer seals the housing around the stoma. In some embodiments of the present methods, the flexible container is coupled to a finger probe, and wherein the method comprises manipulating the finger probe to unblock an obstruction of the stoma. In some embodiments of the present methods, the flexible container comprises a resealable opening, and wherein the method comprises draining the flexible container via the resealable opening.

Some embodiments of the present methods of collecting waste from a stoma of a patient comprise coupling a flexible container to skin surrounding a stoma, wherein the flexible container includes: an first chamber for receiving waste from the stoma; an opening for surrounding at least a portion of the stoma; a second chamber configured to accommodate an absorbent material; and communicating fluid between the second chamber of the housing and a pressure source such that pressure within the second chamber of the housing is sub-atmospheric.

The term "coupled" is defined as connected, although not necessarily directly, and not necessarily mechanically. Two items are "couplable" if they can be coupled to each other. Unless the context explicitly requires otherwise, items that are couplable are also decouplable, and vice-versa. One non-limiting way in which a first structure is couplable to a second structure is for the first structure to be configured to be coupled (or configured to be couplable) to the second structure. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term "substantially" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), and "include" (and any form of include, such as "includes" and "including") are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the apparatuses, systems, and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 is a first perspective view of a first embodiment of the present ostomy apparatuses in a first position, the apparatus being shown with some components hidden.

FIG. 2 is a second perspective view of the apparatus of FIG. 1 in a second position.

FIG. 3 is a top view of a portion of the apparatus of FIG. 1.

FIG. 4 is a cross-section view of a portion of the apparatus of FIG. 1, taken along line 4-4 of FIG. 3.

FIG. 5 is a first perspective view of a second embodiment of the present ostomy apparatuses in a first position, the apparatus being shown with some components hidden.

FIG. 6 is a second perspective view of the apparatus of FIG. 5 in a second position, the apparatus being shown with some components hidden.

FIG. 7 is a third perspective view of the apparatus of FIG. 5 in the second position.

FIG. 8 is a top view of a portion of the apparatus of FIG. 5.

FIG. 9 is a cross-section view of a portion of the apparatus of FIG. 5, taken along line 9-9 of FIG. 8.

DESCRIPTION OF ILLUSTRATIVE EMBODIMENTS

Referring now to the drawings, and more particularly to FIGS. 1-4, shown therein and designated by the reference numeral 100 is one embodiment of the present ostomy apparatuses. FIGS. 1-4 are not drawn to scale. The present ostomy apparatuses (e.g., 100, 100a) may be utilized with any suitable type of ostomy, such as, for example, a colostomy, an ileostomy, urostomy, and/or the like.

Ostomy apparatus 100 comprises a container 102 with an interior cavity 104 for receiving waste from a patient's stoma 106 through an opening 108. For example, as shown, opening 108 of container 102 can be disposed over skin 120 of a patient such that the opening at least partially surrounds stoma 106. In this embodiment, container 102 is flexible (e.g., a bag). Container 102 may be formed of any liquid impermeable material, such as polyvinyl chloride, and may be constructed using any conventional manufacturing technique. In some embodiments, a container (e.g., 102) is assembled using multiple pieces which are solvent welded together. Container 102 may include an antimicrobial agent coated on or embedded in the material. In one embodiment, the antimicrobial agent is silver, such as silver nanoparticles, which have well known antimicrobial properties.

Container 102 may be drainable or disposable. For example, container 102 may include a resealable opening 110 (e.g., in addition to opening 108) for draining the container. Ostomy apparatus 100 may include a finger probe 112 to allow a user to manually manipulate stoma 106. For example, if stoma 106 has a blockage, a user may insert his finger into finger probe 112 and remove the blockage without having to remove container 102. In one embodiment, finger probe 112 comprises an elongated tube which is sealed at one end and open to cavity 104 of container 102 at the other end. Finger probe 112 may be formed of the same material as container 102 and/or may be formed of thinner material to allow easier manipulation or stronger material to withstand repeated manipulation of the material without breakage. When not in use, finger probe 112 may be fastened to container 102 using a refastenable material, such as hook and loop fasteners, adhesive, and/or the like.

Ostomy apparatus 100 includes a locking assembly 114 configured to secure container 102 to skin 120. In this embodiment, locking assembly 114 may comprise a container lock assembly 116 that is coupled to container 102. For example, container lock assembly 116 may be configured to be coupled to opening 108 of container 102. Container lock assembly 116 may comprise one or more retainers, gaskets, rings, and/or the like, one or more of which can include a rigid portion, a pliable portion, a threaded portion, and/or an interlocking portion. For example, suitable container lock assemblies (e.g., 116) are disclosed in paragraphs [0040]-[0043], [0048], [0049] and FIGS. 3 and 9-16 (e.g., see discussion regarding locking retainer 132, flange member 134, and/or ring assembly 220) of U.S. patent application Ser. No. 14/498,117, entitled "Ostomy Bag," which is hereby incorporated by reference in its entirety.

Locking assembly 114 may comprise a stoma lock assembly 118 that is configured to interlock with container lock assembly 116. Stoma lock assembly 118 may comprise one or more retainers, gaskets, rings, and/or the like, one or more of which can include a rigid portion, a pliable portion, a threaded portion, and/or an interlocking portion. For example, suitable stoma lock assemblies (e.g., 118) are disclosed in paragraphs [0038]-[0040], [0045] and FIGS. 3, 6, 9-14 (e.g., see discussion regarding stoma port 118, 210 and gasket 122) of U.S. patent application Ser. No. 14/498,117, entitled "Ostomy Bag."

Locking assembly 114 can be configured to provide fluid communication between stoma 106 and container 102. For example, container lock assembly 116 and stoma lock assembly 118 each comprise a respective opening 122, 124 that is configured to be placed at least partially over patient's stoma 106 such that waste may flow from the stoma, through locking assembly 114, and into cavity 104 of container 102. In this embodiment, container lock assembly 116 can be configured to be coupled to container 102 such that, when the container lock assembly is coupled to stoma lock assembly 118, the container lock assembly seals opening 108 of the container to the stoma lock assembly. In some embodiments, a locking assembly (e.g., 114) can be omitted and an container (e.g., 102) can be coupled to skin (e.g., 120) and seal around a stoma (e.g., 106).

Ostomy apparatus 100 includes an absorbent housing 126. At least a portion of housing 126 may comprise a porous (e.g., polyurethane) material that allows fluid transfer through the material. In some embodiments, at least a portion of housing (e.g., 126) comprises a non-porous (e.g., polyurethane) material that prevents fluid transfer through the material. As shown, housing 126 can be configured to be coupled to locking assembly 114. More particularly, housing 126 can be configured to be coupled to stoma lock assembly 118. In some embodiments, a locking assembly (e.g., 114) can be omitted and an absorbent housing (e.g., 126) can be coupled directly to a container (e.g., 102). In some embodiments, a locking assembly (e.g., 114) can be omitted and an absorbent housing (e.g., 126) can be unitary with a container (e.g., 102), such that, for example, the container includes the housing.

In the depicted embodiment, housing 126 defines a chamber 128 that surrounds stoma 106. An absorbent material 130 can be disposed within chamber 128 of housing 126. As described below, absorbent material 130 may be configured to provide suction against skin 120 and/or an adhesive layer (e.g., 138) between housing 126 and the skin such that stoma lock assembly 118 securely attaches to the skin.

Absorbent material 130 may include an open cell structure, such as an open cell structure comprising a foam- or sponge-like material. In this embodiment, absorbent material 130 may comprise a polyurethane foam. For example, absorbent material 130 may comprise foam bolster material suitable for use in negative-pressure wound therapy, such as, for example, in PREVENA™ Therapy Dressing, which is available from Acelity, Inc. (San Antonio, Tex.).

In this embodiment, housing 126 can be in fluid communication with a pressure source 132. Pressure source 132 may comprise any suitable pump, such as, for example, an electric pump and/or a manual pump. Pressure source 132 is configured to provide a sub-atmospheric pressure within housing 126. More particularly, as discussed in further detail below, pressure source 132 is configured to provide a sub-atmospheric pressure on absorbent material 130 within housing 126 such that the absorbent material removes fluid from skin 120 surrounding stoma 106. In this embodiment, by providing a sub-atmospheric pressure on absorbent material 130, the absorbent material may exert a suction force on skin 120 and/or on an adhesive layer (e.g., 138) disposed between housing 126 and the skin (as described in further detail below) surrounding stoma 106, thereby securing apparatus 100 to the skin. Further, by providing a sub-atmospheric pressure on absorbent material 130, housing 126 can conform to various skin typography and provide a secure seal against skin 120. Ostomy apparatus 100 may comprise a port 134 configured to provide fluid communication between housing 126 (e.g., and/or absorbent material 130 within the housing) and pressure source 132. In this embodiment, port 134 is isolated from fluid communication with respective openings 122, 124 of stoma lock assembly 118 and container lock assembly 116. Ostomy apparatus 100 may include a valve 136 configured to control fluid communication between housing 126 (e.g., port 134) and pressure source 132.

Ostomy apparatus 100 can be configured to include an adhesive layer 138. For example, layer 138 may be configured to be disposed between housing 126 and skin 120 such that the layer adheres the housing to the skin. In some embodiments, an adhesive layer (e.g., 138) can be omitted and a housing (e.g., 126) may be directly coupled to skin (e.g., 120). At least a portion of layer 138 can be non-porous such that fluid transfer through the layer is substantially prevented. In some embodiments, at least a portion of an adhesive layer (e.g., 138) is porous such that fluid can be transferred through the layer. For example, in embodiments where at least a portion of an adhesive layer (e.g., 138) is porous and at least a portion of a housing (e.g., 126) is porous, by providing a sub-atmospheric pressure on an absorbent material (e.g., 130) within the housing, the absorbent material removes fluid from skin (e.g., 120) surrounding a stoma (e.g., 106). Layer 138 can be configured to seal container 102 around stoma 106 such that, when fluid exits stoma 106, the fluid does not leak between skin 120 and housing 126 and/or between locking assembly 114 (e.g., stoma lock assembly 118) and the housing. In some embodiments, stoma paste and/or similar material may be used to seal openings which remain between housing 126 and skin 120. In this way and others, stoma lock assembly 118, via secure contact between skin 120 and housing 126, may be left in place for an extended period of time, such as several days. This allows a patient to conveniently change container 102 without the time-consuming process of preparing the surrounding skin 120 and adhering a new container directly to the prepared skin 120.

Referring now to FIGS. 5-9, shown therein and designated by the reference numeral 100a is a second embodiment of the present ostomy apparatuses. FIGS. 5-9 are not drawn to scale. Apparatus 100a can be substantially similar to apparatus 100, with the primary exceptions described below. For example, in this embodiment, apparatus 100a includes a container lock assembly 116 coupled to an absorbent housing 126 (e.g., "upper housing"), which is configured to hold an absorbent material 130. Container lock assembly 116 may be coupled to stoma lock assembly 118 such that upper housing 126, which is coupled to the container lock assembly, and housing 126 (e.g., "lower housing"), which is coupled to the stoma lock assembly, may be in fluid communication. For example, in this embodiment, a cover 140 may be coupled to both upper housing 126 and lower housing 126 such that the cover seals both housings against skin 120 surrounding stoma 106.

Cover 140 may include a material having an adhesive layer configured to adhere to upper housing 126 and/or lower housing 126. As shown, cover 140 may be configured to wrap around at least a portion of the peripheral edge of upper housing 126 and/or lower housing 126. Cover 140 may be configured to wrap around at least a portion of an upper surface of upper housing 126. In this embodiment, port 134 is configured to provide fluid communication between pressure source 132 and both upper housing 126 and lower housing 126. For example, by providing a sub-atmospheric pressure within upper housing 126, the upper housing exhibits a suction force on lower housing 126 and thereby provides a more secure connection between the housings, and thus, a more secure connection between container lock assembly 116 and stoma lock assembly 118.

Some embodiments of the present methods of collecting waste from a stoma (e.g., 106) of a patient include adhering an adhesive layer (e.g., 138) to skin (e.g., 120) surrounding the stoma; coupling a housing (e.g., 126) to the adhesive layer, the housing including: a chamber (e.g., 128); and an absorbent material (e.g., 130) disposed within the chamber; coupling a flexible container (e.g., 102) to the housing (e.g., by a locking assembly (e.g., 114)), wherein the flexible container includes an interior chamber (e.g., 104) for receiving waste from the stoma and an opening (e.g., 108) for surrounding at least a portion of the stoma; communicating fluid between the housing and a pressure source (e.g., 132) such that pressure within the chamber is sub-atmospheric. In some embodiments of the present methods, the adhesive layer seals the housing around the stoma. In some embodiments of the present methods, the flexible container is coupled to a finger probe (e.g., 112) and the method comprises manipulating the finger probe to unblock an obstruction of the stoma. In some embodiments of the present methods, the flexible container comprises a resealable opening (e.g., 110) and the method comprises draining the flexible container via the resealable opening.

The apparatuses (e.g., 100, 100a) disclosed herein include the benefits of providing a more secure and/or conforming seal between skin 120 and the apparatus, which may allow patients with physically active lifestyles a greater freedom of movement and convenience.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. An ostomy apparatus comprising:
    an ostomy bag comprising:
        a flexible container having:
            an interior chamber configured to receive waste from a patient's stoma,
            a first end defining a first opening configured to surround the stoma and receive the waste into the interior chamber; and
            a first locking ring coupled to the first end of the flexible container;
    a wafer configured to accommodate an absorbent material that surrounds the stoma, the wafer comprising:
        a second locking ring configured to engage with the first locking ring to couple the ostomy bag to the wafer;
        a second opening configured to surround the stoma and receive the waste from the stoma and into the interior chamber while the first and second locking rings are engaged;
        a port provided in the wafer and configured to provide fluid communication between an interior of the wafer and a pressure source, wherein the port is isolated from fluid communication with the first and second openings; and
    an adhesive layer having a first side coupled the wafer and a second side configured to be coupled to skin to seal the wafer to the skin around the stoma.

2. The apparatus of claim 1, further comprising a finger probe coupled to the flexible container, the finger probe being configured to allow a user to manipulate the stoma.

3. The apparatus of claim 1, wherein the container has a resealable opening for draining the container.

4. The apparatus of claim 1, wherein the absorbent material includes an open cell structure.

5. The apparatus of claim 1, where:
    the first locking ring is configured to engage the second locking ring such that the first and second locking rings cooperate to define a passage extending between a first end and a second end of the wafer.

6. The apparatus of claim 1, wherein the port is coupled to a side surface of the wafer.

7. The apparatus of claim 6, wherein the interior of the wafer includes an annular chamber and the absorbent material is disposed within the annular chamber.

8. An ostomy apparatus comprising:
    an ostomy bag comprising:
        a flexible container having a receptacle for receiving waste from a patient's stoma and;
        a first lock assembly defining a first opening configured to surround the stoma and receive the waste into the receptacle; and
    a wafer configured to surround the stoma and accommodate an absorbent material, the wafer comprising:
        a second lock assembly configured to engage with the first lock assembly to couple the ostomy bag to the wafer;
        a second opening configured to surround the stoma and receive the waste from the stoma and into the receptacle when the first and second lock assemblies are engaged;
        a port provided in the wafer and configured to provide fluid communication between an interior of the wafer and a pressure source, wherein the port is isolated from fluid communication with the first and second openings; and an adhesive layer configured to couple the wafer to skin surrounding the stoma.

9. The apparatus of claim 8, wherein the pressure source is configured to provide a sub-atmospheric pressure within an interior of the wafer.

10. The apparatus of claim 8, wherein the pressure source is configured to provide a sub-atmospheric pressure on the absorbent material such that the absorbent material removes fluid from skin surrounding the stoma.

11. The apparatus of claim 8, further comprising a valve being configured to control fluid communication between the wafer and the pressure source.

12. The apparatus of claim 8, wherein the first lock assembly is configured to engage the second lock assembly to form a passageway between the stoma and the receptacle.

13. The apparatus of claim 12, wherein the adhesive layer includes a first side coupled to a first end of the wafer and a second side configured to be coupled to skin to seal the wafer to the skin around the stoma.

14. A method of collecting waste from a stoma of a patient, the method comprising:

adhering an adhesive layer to skin surrounding the stoma;

coupling a wafer to the adhesive layer, the wafer including:

an interior chamber;

an absorbent material disposed within the chamber;

a wafer locking assembly having a first opening; and a port provided in the wafer and configured to provide fluid communication between the interior chamber and a pressure source;

coupling an ostomy bag having a flexible container and a container locking assembly to the wafer such that the wafer locking assembly engages the container locking assembly, wherein the flexible container includes a receptacle configured to receive waste from the stoma and a second opening for surrounding at least a portion of the stoma; and communicating fluid between the chamber of the wafer and a pressure source such that pressure within the chamber of the wafer is sub-atmospheric;

wherein the port is isolated from fluid communication with the first and second openings.

15. The method of claim 14, wherein the adhesive layer seals the housing wafer around the stoma.

16. The method of claim 14, wherein the flexible container is coupled to a finger probe, and wherein the method comprises manipulating the finger probe to unblock an obstruction of the stoma.

17. The method of claim 14, wherein the flexible container comprises a resealable opening, and wherein the method comprises draining the flexible container via the resealable opening.

18. The apparatus of claim 8, wherein:

the wafer includes:

an inner wall that defines an inner perimeter; and an outer wall that defines an outer perimeter having a larger transverse dimension than the inner perimeter; and the port is included in the outer wall of the wafer.

19. The apparatus of claim 8, wherein the adhesive layer is configured to be coupled to the skin to seal the wafer to the skin around the stoma that is surgically created and disposed outside of a wound bed.

* * * * *